(12) United States Patent
Kozak

(10) Patent No.: US 6,313,106 B1
(45) Date of Patent: Nov. 6, 2001

(54) PHOSPHOLIPID DERIVATIVES OF VALPROIC ACID AND MIXTURES THEREOF

(75) Inventor: Alexander Kozak, Rehovot (IL)

(73) Assignee: D-Pharm Ltd., Rehovot (IL)

(*) Notice: Subject to any disclaimer, the term of this patent is extended or adjusted under 35 U.S.C. 154(b) by 0 days.

(21) Appl. No.: 09/614,271

(22) Filed: Jul. 12, 2000

Related U.S. Application Data

(62) Continuation-in-part of application No. 09/428,848, filed on Oct. 28, 1999, which is a continuation of application No. 08/479,959, filed on Jun. 7, 1995, which is a continuation-in-part of application No. 08/481,243, filed as application No. PCT/GB94/00669 on Mar. 30, 1994, now Pat. No. 5,985,854.

(51) Int. Cl.$^7$ .................................................. A61K 31/685
(52) U.S. Cl. ............................ 514/77; 514/76; 514/114; 514/117; 514/143; 514/144; 514/526; 554/78; 554/79; 554/80
(58) Field of Search .......................... 554/78, 79, 80; 514/76, 77, 114, 117, 143, 144, 826

(56) References Cited

U.S. PATENT DOCUMENTS

| | | | |
|---|---|---|---|
| 5,149,794 | 9/1992 | Yatvin et al. | 536/26.8 |
| 5,227,514 | 7/1993 | Meul et al. | 560/67 |
| 5,985,854 | 11/1999 | Kozak | 514/75 |
| 6,077,837 | 6/2000 | Kozak | 514/77 |

FOREIGN PATENT DOCUMENTS

| | | |
|---|---|---|
| 0679856 | 4/1992 | (CH). |
| 0275005 | 7/1988 | (EP). |
| 0325160 | 7/1989 | (EP). |
| 3133987 | 6/1991 | (JP). |
| 8905358 | 6/1989 | (WO). |
| 9000555 | 1/1990 | (WO). |
| 9010448 | 9/1990 | (WO). |
| 9116920 | 11/1991 | (WO). |
| 9300910 | 1/1993 | (WO). |
| 9408573 | 4/1994 | (WO). |

OTHER PUBLICATIONS

"Prodrugs Based on Phospholipid–Nucleoside Conjugates." NITS Technical Notes, No. 9, p. 630 (1984).

O. Vaizoglu, et al., European J. Pharmaceutics and Biopharmaceutics, 38(1): Jul. 1–6, 1989.

Hoestetler, et al., "Phosphatidylazothymidine. Mechanism of Antiretroviral Action in Stem Cells." J. Bio. Chem. 266 (18): 11714–7–15 Jun., 1991.

Gusovsky, et al., "Mechanism of Maitotoxin–Stimulated Phosphoinositide Breakdown in HL–60 Cells." J. Pharmacol. Ex. Ther. 252(2):469–470. Feb., 1990.

Govez–Cambronero, et al., "Platelet–Activating Factor Induces Tyrosine Phosphorylation in Human Neutrophils." J. Biol. Chem. 266(10):6240–45. Apr., 1991.

Primary Examiner—Deborah D. Carr
(74) Attorney, Agent, or Firm—Davidson, Davidson & Kappel, LLC

(57) ABSTRACT

The present invention relates to compounds, which are phospholipid derivatives of valproic acid, to compositions comprising said compounds and their use for treating epilepsy, migraine, bipolar disorders and pain.

34 Claims, 2 Drawing Sheets

FIG. 2
FIG. 2A
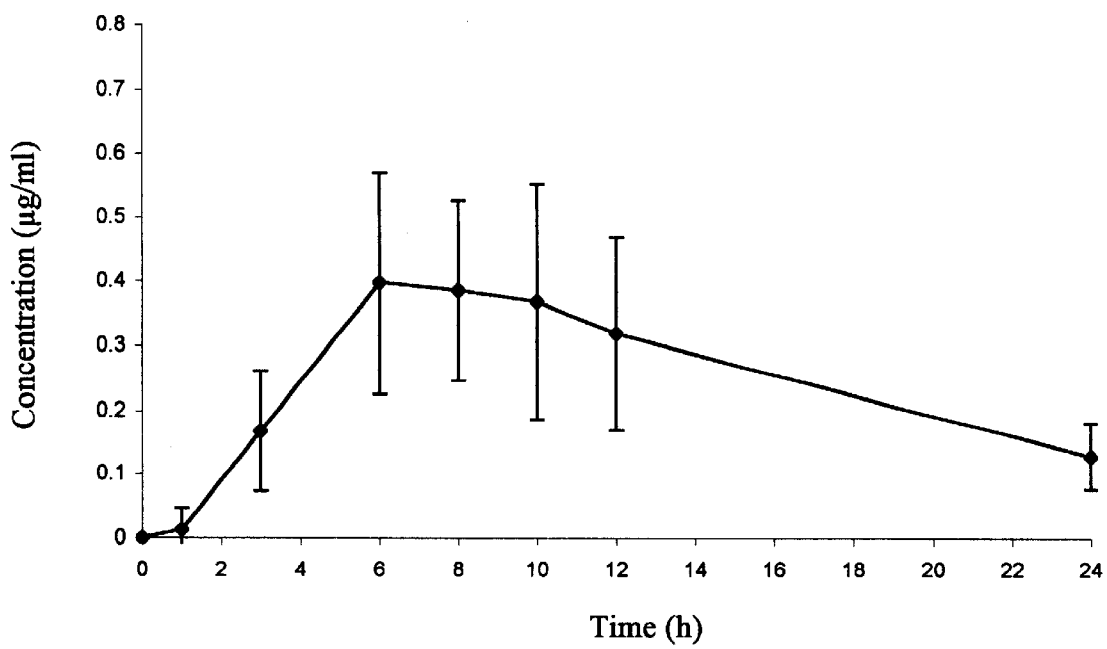
FIG. 2B
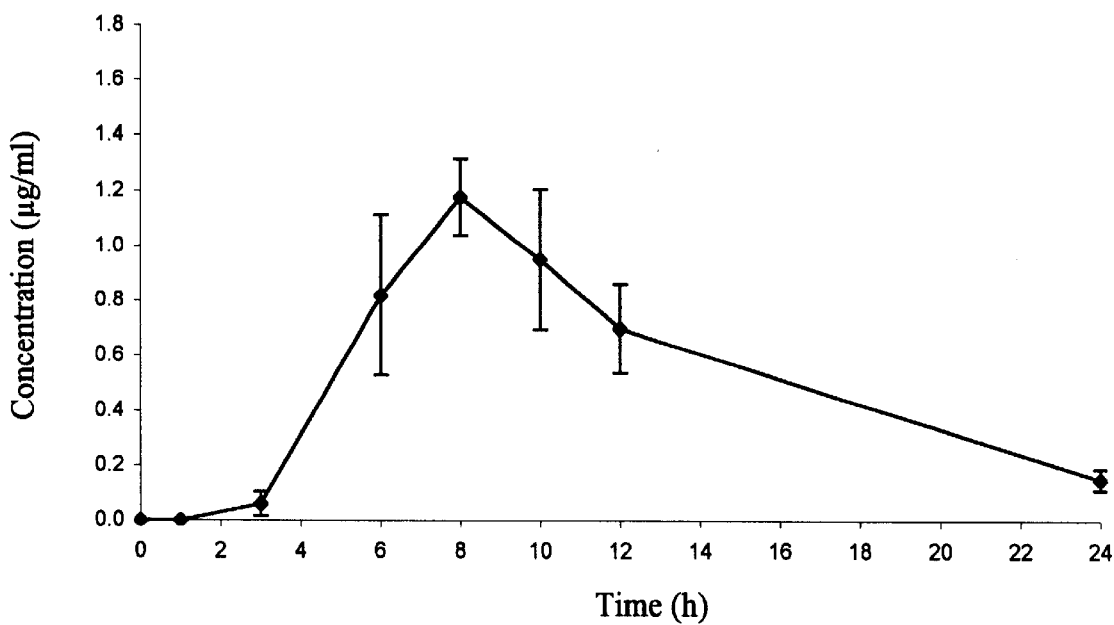

ns to compounds, which are
PHOSPHOLIPID DERIVATIVES OF VALPROIC ACID AND MIXTURES THEREOF This application is a continuation-in part of U.S. patent application Ser. No. 09/428,848, filed on Oct. 28, 1999, which is a continuation of U.S. patent application Ser. No. 08/479,959, filed on Jun. 7, 1995, which is a continuation-in part of U.S. patent application Ser. No. 08/481,243, filed on Aug. 21, 1995 U.S. Pat. No. 5,935,354 as a U.S. national stage application of PCT/GB94/00669 filed Mar. 30, 1994, and U.S. No. 5,985,854, The disclosures of each of these applications is herein incorporated by reference.

FIELD OF THE INVENTION

The present invention relates to compounds, which are phospholipid derivatives of valproic acid, to compositions comprising said compounds and their use for treating epilepsy, migraine, bipolar disorders and pain.

BACKGROUND OF THE INVENTION

Epilepsy is a neurological disease that is characterized by paroxysmal transient disturbances of the electrical activity of the brain. Epileptic seizures may be partial or focal seizures that are restricted to a particular locus within the brain, or generalized seizures which can result in abnormal activity throughout the brain. The disturbances of brain function during an epileptic attack may be manifested as psychic or sensory incidents such as amnesia, hallucinations, deja vu states etc., as abnormal motor phenomenon such as spasms or whole body convulsions or as loss of consciousness. In extreme cases, epilepsy can degenerate into status epilepticus which may be fatal (DeLorenzo et al.—J. Clin. Neurophysiol. (1995) 12: 316–325).

Valproic acid (VPA) and its sodium salt (sodium valproate, NaVPA) are among the most prescribed anti-epileptic drugs. These drugs are also effective in the treatment of bipolar disorders and in prophylaxis of migraines.

Although the clinical usefulness of valproic acid is well established, this compound suffers major drawbacks. Treatment with VPA is associated with adverse side effects such as gastro-intestinal irritation, bone marrow suppression (especially manifested as aplastic anemia and thrombocytopenia), and hepatic dysfunction. VPA has also been reported to have teratogenic effects and patients treated with VPA may experience nausea, vomiting, dizziness, confusion or sedation.

Another drawback of valproic acid is its short half-life due to rapid clearance of the drug. As a result plasma levels of VPA fluctuate during chronic treatment and the drug has to be administered several times a day even as a sustained release formulation. In addition, valproic acid, which is a liquid, is less desirable for use as an oral dosage form. The sodium valproate, on the other hand, is solid, but being hygroscopic is characterized by poor stability.

Efforts have been made in order to overcome the VPA-induced side effects and the disadvantageous physical and pharmacokinetic properties of the drug. Most approaches that have been taken involve modification of the VPA molecule. However, although some of the modified drugs were devoid of adverse side effects, in many cases they also lost the therapeutic effect or were much less potent.

Mergen et al (J. Pharm. Pharmacol. (1991), 43: 815–816) describe conjugates of valproic acid with 1,3-dipalmitoylglycerol, 1,2-dipalmitoylglycerol or 1,3-diaminopalmitoyl-propan-2-ol. According to the Mergen et al.'s publication, only the latter compound was found to have antiepileptic activity, while both conjugates of VPA with the diglycerides were inactive.

Hadad et al. (Biopharmaceutics & Drug Disposition (1993), 14: 51–59) investigated the anticonvulsant activity of 1,4-butanediol divalproate, glyceryl trivalproate and valpromide in comparison to valproic acid. Their study demonstrated that only 1,4-butanediol divalproate, in one of the model systems tested, had a better protective index value than VPA.

U.S. Pat. No. 4,654,370 to Marriott and Paris discloses glycerides esterified with one or two moles of valproic acid. These compounds have been found to have the same useful therapeutic effect as valproic acid alone but without causing gastric irritation.

U.S. Pat. Nos. 4,988,731 and 5,212,326 both to Meade, disclose oligomers having 1:1 molar ratio of sodium valproate and valproic acid which have physiological properties similar to those of valproic acid or sodium valproate but show superior stability characteristics.

U.S. Pat. No. 4,558,070 to Bauer and Shada discloses a stable complex between valproic acid and potassium, cesium or rubidium which may be formed by combining four moles of valproic acid with one mole of the alkali metal ion. The alkali metal salts of valproic acid were reported to have improved stability.

Despite continuous efforts in the field, it is still an unmet need to provide an anti-epileptic medication with improved pharmacokinetic properties and overall superior therapeutic index.

SUMMARY OF THE INVENTION

The present invention provides pharmaceutical compositions comprising, as an active ingredient, a compound comprising valproic acid or a pharmaceutically acceptable derivative thereof which is covalently bonded to a phospholipid moiety. In preferred embodiments of the invention, the phospholipid moiety is selected from plasmalogens, phosphatidic acids and phosphoglycerides. More preferred are compounds, wherein said phospholipid moiety is lysophosphatidyl-ethanolamine, N-mono-($C_{1-4}$)-alkyl, N,N-di-($C_{1-4}$)-alkyl and quaternary derivatives of the amines thereof.

Most preferred embodiments, in accordance with the invention, are compositions comprising phospholipid derivatives of valproic acid (hereinafter referred to as DP-VPA) wherein valproic acid is covalently linked as an ester at the sn-2 position of a phospholipid moiety.

Currently the most preferred DP-VPA compounds are 1-Palmitoyl-2-valproyl-sn-glycero-3-phosphatidylcholine, also referred to as 1-hexadecanoyl-sn-glycero-3-phosphorylcholine (hereinafter denoted as $C_{16}$-DP-VPA) and 1-Stearoyl-2-valproyl-sn-glycero-3-phosphatidylcholine, also referred to as 1-octadecanoyl-sn-glycero-3-phosphorylcholine (hereinafter denoted as $C_{18}$-DP-VPA).

According to preferred embodiments of the present invention, the pharmaceutical compositions comprise a mixture of DP-VPA compounds, more preferably a mixture of $C_{16}$-DP-VPA and $C_{18}$-DP-VPA (hereinafter denoted as $C_{16}$/$C_{18}$-DP-VPA).

In one preferred embodiment the ratio of $C_{16}$-DP-VPA to $C_{18}$-DP-VPA in the $C_{16}$/$C_{18}$-DP-VPA mixture is from around 1:20 to around 1:2 by weight. Most preferred are mixtures wherein the ratio of $C_{16}$-DP-VPA to $C_{18}$-DP-VPA is from around 1:5 to around 1:7 w/w (equivalent to 15±5% $C_{16}$-DP-VPA: 85±5% $C_{18}$-DP-VPA (w/w)).

The compounds and compositions of the invention are useful for the treatment of central nervous system disorders including, but not limited to, epilepsy, migraines, chronic pain and bipolar disorders.

Thus, according to yet another embodiment of the present invention, there is provided a method for the treatment of a central nervous system disorder in a subject, comprising the step of administering to a patient in need thereof a therapeutically effective amount of a compound or a pharmaceutical composition in accordance with the invention.

Further objects of the present invention will become apparent to those skilled in the art upon further review of the following disclosure, including the detailed descriptions of specific embodiments of the invention.

BRIEF DESCRIPTION OF THE DRAWINGS

FIGS. 2A–B depict plasma concentrations of $C_{16}$-DP-VPA (2A) and $C_{18}$-DP-VPA (2B) measured at different time points following a single oral administration to human subjects of 0.625 g of $C_{16}$/$C_{18}$-DP-VPA ($C_{16}$/$C_{18}$ ratio= 13%:87% w/w).

DETAILED DESCRIPTION THE INVENTION

Figure 1:
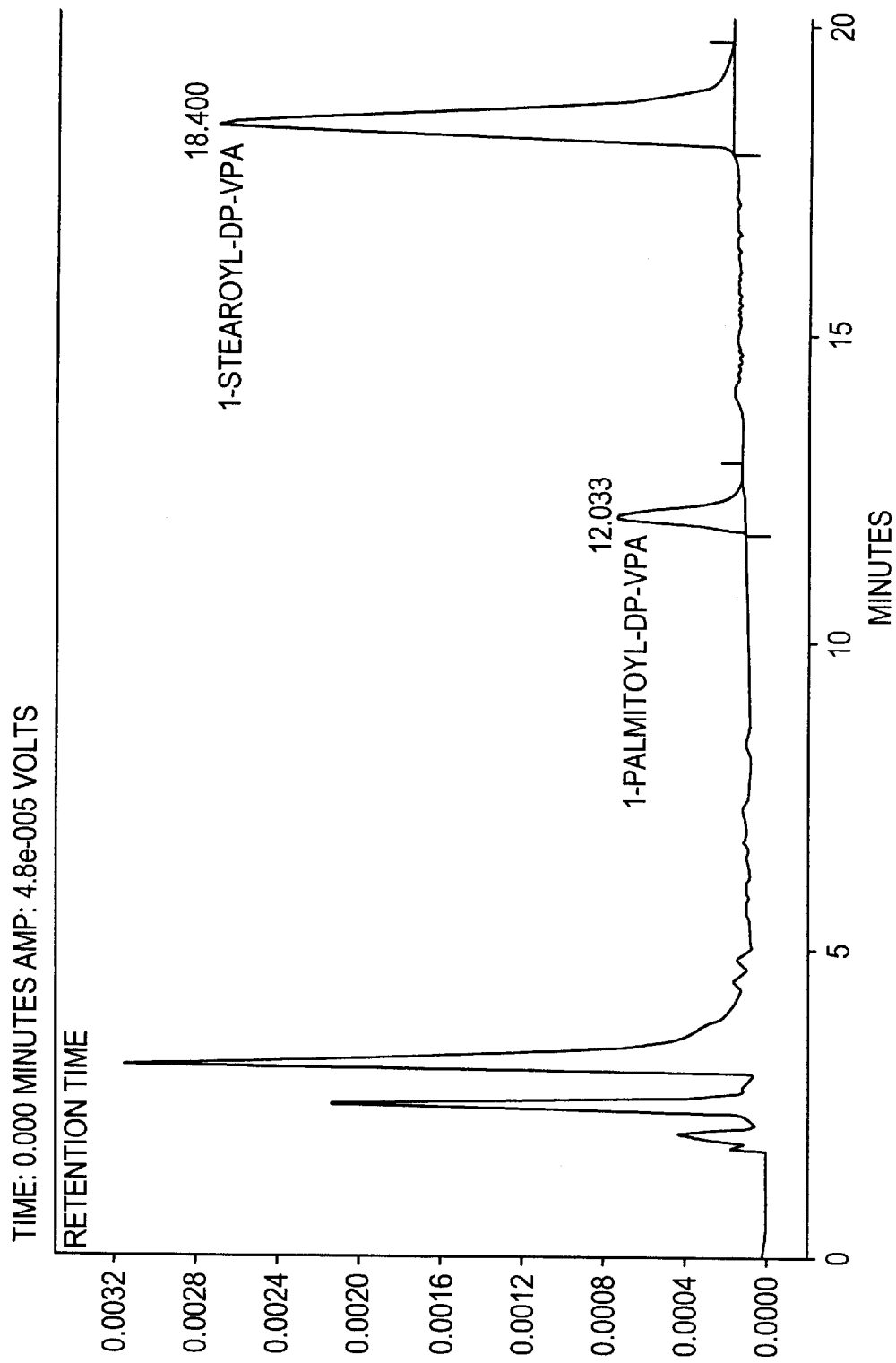
FIG. 1 depicts a typical HPLC chromatogram of a $C_{16}$/$C_{18}$-DP-VPA composition, where the $C_{16}$-DP-VPA to $C_{18}$-DP-VPA ratio is 15%:85%, by weight

The present invention relates to phospholipid derivatives of valproic acid, to pharmaceutical compositions comprising these compounds and mixtures thereof, and to their use in the treatment of neurological disorders.

DP-VPA molecules are disclosed in U.S. patent application Ser. No. 08/479,959 and International Patent Publication WO 94/22483, the disclosure of which is herein incorporated by reference.

Specifically disclosed in the abovementioned applications is a molecule, referred to as "TVA 16", which is a 1:1 ester of valproic acid with 1-hexadecanoyl-sn-glycero-3-phosphorylcholine. TVA 16 was shown to have significant anticonvulsant activity and to be more potent than sodium valproate. In the present application, the 1:1 ester of valproic acid with 1-hexadecanoyl-sn-glycero-3-phosphorylcholine, or in its chemical name 1-Palmitoyl-2-valproyl-sn-glycero-3-phosphatidylcholine, is hereinafter referred to as $C_{16}$-DP-VPA.

Another embodiment, disclosed in the present application, is a 1:1 ester of valproic acid with 1-octadecanoyl-sn-glycero-3-phosphorylcholine, or in its chemical name 1-Stearoyl-2-valproyl-sn-glycero-3-phosphatidylcholine. This molecule is hereinafter referred to as $C_{18}$-DP-VPA.

The DP-VPA compounds of the invention include conjugates of valproic acid, or a pharmaceutically acceptable derivative thereof, with any phospholipid, preferably a phosphoglyceride. Suitable phospholipids include, but are not limited to, plasmalogens, phosphatidic acids and phosphoester derivatives thereof. Preferred phospholipid moieties, in accordance with he invention, include lysophosphatidylethanolamine, N-mono-($C_{1-4}$)-alkyl, N,N-di-($C_{1-4}$)-alkyl and quaternary derivatives of the amines thereof. Currently, the most preferred phospholipid in the compounds of the invention is phosphatidylcholine.

The choice of the fatty acid residue at position sn-1 of a glycero-phospholipid moiety is specifically discussed below in connection with the preferred compounds in accordance with the invention. However, it should be appreciated that VPA or its pharmaceutically acceptable derivative may be covalently linked to the phospholipid moiety at positions sn-1, sn-2 or linked to the phospholipid head group at position sn-3. Accordingly, it is possible that VPA or its derivative is released by cleavage by the respective phospholipases, $PLA_1$, $PLA_2$, PLC and PLD as depicted in the following scheme 1.

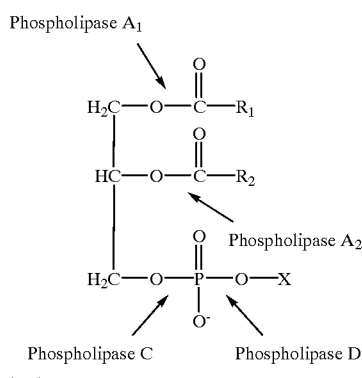

X = H or a polar head group.

In preferred embodiments of the invention, VPA, or its pharmaceutically acceptable derivative, is joined to the phospholipid via an ester linkage at position sn-2, thus enabling release of VPA by phospholipases $A_2$. In particularly preferred embodiments, VPA is covalently linked by an ester bond to the sn-2 position of phoshatidylcholine.

The term "pharmaceutically acceptable derivatives of VPA" as used in the specification refers to pharmaceutically acceptable analogs of valproic acid having similar therapeutic activity. This includes derivatives of VPA with saturated or unsaturated carbon chains having one or more double and/or triple bonds. Pharmaceutically acceptable substituent on the carbon atoms of the molecules are also allowed and may include, for example, halogen atoms or lower alkyl groups comprising 1–5 carbon atoms. Amides of VPA and its analogs as mentioned above are also included within the scope of the invention. Furthermore, for those compounds having a chiral centre of asymmetry, the compounds of the present invention include optically active isomers, racemates or preferred mixtures thereof.

It should be appreciated that within the scope of the invention are also pharmaceutically acceptable salts of the DP-VPA compounds. The term "pharmaceutically acceptable salts" means non-toxic salts of the compounds of the invention including, but not limited to, sodium, potassium, calcium, magnesium, ammonium, alkyl ammonium or amine derived salts.

Although both $C_{18}$-DP-VPA and $C_{16}$-DP-VPA are potent anticonvulsant agents having similar efficacies, it has now been unexpectedly found that the two compounds differ in their pharmacokinetic profiles. The $C_{16}$-DP-VPA compound, following a single oral administration, exhibits a significantly prolonged half-life in plasma in comparison to the half-life of $C_{18}$-DP-VPA. However, the plasma concentrations of $C_{18}$-DP-VPA were found to reach peak levels at a later time point in comparison to the peak levels of the $C_{16}$-DP-VPA molecule.

It is now disclosed, for the fist time, that mixtures Of $C_{16}$-DP-VPA and $C_{18}$-DP-VPA (herein referred to as $C_{16}$/$C_{18}$-DP-VPA) offer an advantage by exhibiting higher therapeutic effect and prolonged therapeutic effect in comparison to the effect of compositions comprising either $C_{16}$-DP-VPA or $C_{18}$-DP-VPA alone.

Preferred compositions, in accordance with the invention, are those wherein the $C_{16}$-DP-VPA to $C_{18}$-DP-VPA ratio in the $C_{16}/C_{18}$-DP-VPA mixture is from around 1:20 to around 1:2 (by weight). Most preferred are mixtures wherein the ratio of $C_{16}$-DP-VPA to $C_{18}$-DP-VPA is around 15±5%: 85±5% (w/w).

Without wishing to be limited to a single mechanism or theory, it is suggested that the length of the alkyl moiety esterified at position sn-1 of the phospholipid may determine the lipophilicity of the DP-VPA molecule, and thus also its transport across cellular membranes.

Alternatively, again without wishing to be limited to a single mechanism or theory, the fatty acid residue at position sn-1 may determine the properties of the DP-VPA conjugate as a substrate for phospholipases, thus affecting the regulated release of valproic acid, for example, by elevated activity of phospholipase $A_2$ (PLA$_2$) at the diseased site. Phospholipases $A_2$ are a family of esterases that hydrolyze the sn-2 ester bonds in phosphoglyceride molecules. It has been shown that in disorders such as epilepsy, PLA$_2$ activation coincides with epileptic seizures (Flynn and Wecker (1987) J. Neurochem. 48: 1178–84; Bazan, et al. (1986) Adv. Neurol. 44: 879–902).

Also associated with elevated phospholipase $A_2$ activity, are bipolar disorders and some types of pain and migraine that are associated with inflammatory processes (Horrobin and Bennett (1999) Prostaglandins Leukot Essent Fatty Acids 60: 141–167).

The compounds according to the invention, being hydrophobic in nature, may penetrate biological membranes and barriers, thus facilitating the transport of the drug into cells or organs, for example, into the brain where their effect is needed.

It may be envisaged that regulated release of the valproic acid moiety at the diseased target site may even further improve the therapeutic index of the drug, as the efficacy the drug is expected to increase while potential side effects and toxicity are reduced. Valproic acid may be released by cleavage of the DP-VPA compound at position sn-2 of the phospholipid by phospholipase $A_2$ or any other lipase or esterase. However, it may not be excluded that the active drug may be different from the original parent drug molecule, VPA, with a chemical group(s) being removed from or added to its structure while being released from its intracellular transporting adjuvant or as a result of physiological phospholipid metabolism.

It is important to note that the conjugate of the invention, namely the valproic acid or its pharmaceutically acceptable derivative covalently linked to the phospholipid moiety, may be active per se. Alternatively, the covalent bond of the lipid-drug conjugate may, under certain circumstances, be cleaved to release the pharmacologically active drug. In the latter case, the compound of the invention may be regarded as a prodrug, in the sense that the therapeutic agent is released from its transporting adjuvant.

Irrespective of the exact mechanism of action, it is evident that the compounds of the invention have an improved therapeutic profile and are more effective comparing to VPA in at least two aspects: (i) increased efficacy, and (ii) decreased side effects.

The DP-VPA compounds were found to be effective at much lower equivalent molar doses compared to the doses currently used for VPA. The reduced therapeutic doses in turn reduce the toxicological risk, accompanying side effects and also reduce the risk of undesirable interactions with other drugs. In addition, the DP-VPA molecules have been found to exhibit significantly improved pharmacokinetic properties compared to VPA (e.g. substantially increased half-life in serum and in brain tissue). Thus, the DP-VPA molecules represent a class of superior anti-epileptic drugs.

Furthermore, the preferred pharmaceutical compositions in accordance with the invention, i.e. compositions comprising a mixture of both $C_{16}$-DP-VPA and $C_{18}$-DP-VPA, may conveniently be prepared from natural sources.

It would be highly advantageous to have DP-VPA molecules that can be obtained from starting material which can be derived from natural sources by a relatively simple procedure. Such starting material, which is readily available, is lyso-lecithin obtained from egg or soybean lecithins. The soybean, being a non-animal source, is the preferred starting material in the preparation of medicaments for human use. In typical hydrogenated preparations derived from soybean the content of 1-palmitoyl-lysolecithin is around 8–18% and the content of 1-stearoyl-lysolecithin is around 80–90% (by weight).

Pure $C_{16}$-DP-VPA and $C_{18}$-DP-VPA molecules may be chemically synthesized de novo. Alternatively, pure $C_{16}$-DP-VPA and $C_8$-DP-VPA compounds may be prepared by using starting materials obtainable from natural sources, i.e $C_{16}$-lyso-lecithin and $C_{18}$-lyso-lecithin may be isolated and purified, for example, from eggs or soybeans, and then acylated by VPA (=semi-natural preparation).

$C_{16}$-DP-VPA and $C_{18}$-DP-VPA, in particular when used as mixtures within a preferred range of ratios in accordance with the present invention, have been shown, to exhibit significantly improved therapeutic properties. The advantageous properties were exemplified by the substantially increased half-life of DP-VPA in serum and the high efficacy of the drug. The improved residency time in the serum may facilitate the attainment of steady-state drug levels with reduced fluctuation around the therapeutic blood level and reduction in the frequency of drug administration to once or twice per day.

The compositions of the invention can be administered orally, parenterally, (for example by intravenous drip or intraperitoneal, subcutaneous, or intramuscular injection), topically, (for example by nasal application or inhalation) or rectally. Oral administration is a currently more preferred route of administration.

Suitable formulations for administration of the compounds of the invention, whether used separately or as a mixture, include, but are not limited to, powders, granules, emulsions, suspensions or solutions in water or non-aqueous media, in the dosage form of tablets, capsules, syrups or solutions.

For oral administration, DP-VPA amounts of from about 0.5 to 20 mg/kg body weight per day are useful, preferably 1 to 8 mg/kg body weight per day. Dosing will be dependent on the severity of the symptoms and on the responsiveness of the subject to the DP-VPA drug. A physician or other persons of ordinary skill in the art can easily determine optimum dosages and dosage form as well as dosage regimen and means of administration.

The invention will now be illustrated by the following non-limiting examples.

EXAMPLES Example 1

Synthesis of DP-VPA

The synthesis of DP-VPA is a two-stage process. The first stage is aimed at obtaining valproic anhydride by heating of valproic acid in a solution of acetic anhydride under catalysis of pyridine. In the second stage, DP-VPA is prepared by interaction of valproic anhydride with lyso-lecithin. This reaction is conducted in a solution of valproic anhydride by catalysis of 4-dimethylaminopyridine at 90–100° C.

Extraction and purification of the product obtained are carried out in four stages. The first stage of purification is performed by extraction of the un-reacted valproic anhydride, valproic acid and catalyst (4-aminopyridine) in acetone. The crude product obtained is precipitated and separated from solution at the second stage. The solid product obtained is washed from the remaining compounds at the third stage. Finally, the product is re-crystallized several times from an acetone/ethanol solution and the residual solvents are removed under vacuum. Yield of the product is around 80%.

Scheme of synthesis of $C_{18}$-DP-VPA

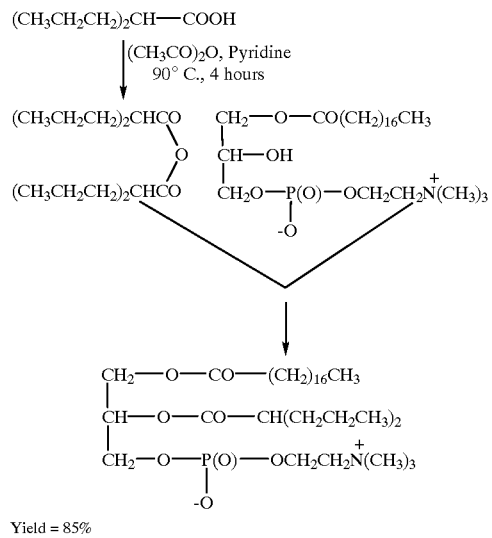

Yield = 85%

The 1-Palmitoyl-2-valproyl-sn-glycero-3-phosphatidylcholine ($C_{16}$-DP-VPA) and 1-Stearoyl-2-valproyl-sn-glycero-3-phosphatidylcholine ($C_{18}$-DP-VPA) compounds were prepared using, respectively, lyso-stearic- and lyso-palmitic- phophatidycholines.

The lyso-stearic- and lyso-palmitic-phophatidycholines may be purified from a natural source (e.g. egg or soybean) by means and procedures well known in the art (F. Gunstone (1999) Fatty Acid and Lipid Chemistry, pp. 87–99, Aspen Publishers, Inc.).

Alternatively these starting materials may be obtained by chemical synthesis procedures as known in the art.

Example 2
Synthesis of $C_{16}/C_{18}$-DP-VPA

Mixtures of $C_{16}/C_{18}$-DP-VPA were prepared by the same procedure as described in Example 1 for the preparation of DP-VPA. The difference was that in the case of the mixture compositions the interaction of valproic anhydride was with lyso-lecithin, which was obtained from soybean and saturated by hydrogenation (S VPC-3 from Lipoid GmbH, Ludwigshafen, Germany).

Example 3
Analysis of DP-VPA compounds $C_{16}/C_{18}$-DP-VPA mixtures synthesized as described above in Example 2 were subjected to analytical assays for characterization and proof of structure. Analytical results of a product containing 1-Palmitoyl-2-valproyl-sn-glycero-3-phosphatidylcholine ($C_{16}$-DP-VPA) and 1-Stearoyl-2-valproyl-sn-glycero-3-phosphatidylcholine ($C_{18}$-DP-VPA), at a ratio of 13%:87% (by weight) are given below.

Mass Spectroscopy

The mass of the protonated DP-VPA molecules as determined by ESI (+) is 622.4 to 622.8 for $C_{16}$-DP-VPA, and 650.4 to 650.8 for $C_{18}$-DP-VPA.

This agrees well with the calculated molecular weight values.

Elementary Analysis

Calculated for $M.H_2O$: C 60.93%, H 10.25%, N 2.11%, P 4.66% (M is corrected for the content of 1-palmitoyl-2-valproyl-sn-glycero-3-phosphatidylcholine).

The average values found were C 60.72%, H 10.58%, N 2.09%, P 4.56%.

These values agree well with the calculated values.

Thin layer Chromatography (TLC) analysis

A TLC is performed on silica gel 60 $F_{254}$ on aluminium sheet with a chloroform:methanol:water (65:35:5, v/v) fluent. The spray reagent for detection is a mixture of 4-methoxybenzaldehyde (5ml), sulphuric acid 95–98% (5 ml), ethanol (100 ml) and glacial acetic acid (1 ml). The sheet is sprayed with this reagent and then heated with hot air at 120–150° C.

The TLC analysis results show that there is one spot at an $R_f$ of 0.58 to 0.60.

Analytical NMR Data

The typical NMR data given below are for proton, carbon-13 and phosphorus-3 1. $^1H$ NMR($CDCl_3$), δ (ppm): 0.84–0.90 (m, 9H), 1.24–1.27 (broad s)+1.31–1.41 (m) (both 34H), 1.50–1.59 (m, 4H), 2.21–2.28 (t, 2H), 2.29–2.37 (m, 1H), 3.35 (s, 9H), 3.77–3.78 (broad s, 2H), 3.88–3.96 (m,2H), 4.06–4.14 (m, 1H), 4.30 (broad s, 2H), 4.40–4.46 (d, 1H), 5.18 (m, 1H). $^{13}C$ NMR($CDCl_3$), δ (ppm): 8.62 ($CH_3$), 22.65 ($CH_3$), 62.99 [($CH_3$)$_3$N],29.17, 30.93, 33.15, 39.92, 43.07, 53.86, 67.97, 71.89, 74.99, 78.91 ($CH_2$ and CH), 182.21 (CO), 184.43 (CO). $^{31}P$ NMR($CDCl_3$), δ (ppm): -0.29 (respectively to $H_3PO_4$ in $D_2O$).

HPLC Analysis

DP-VPA is analysed by HPLC using the following conditions:

| Instrument: | Liquid chromatograph equipped with integrating device |
|---|---|
| Column: | Zorbax Eclipse XDB C18, 5μ, 4.6 × 250 mm |
| Mobile phase: | Methanol - Acetonitrile - Water (85:15:5 v/v) |
| Flow rate: | 1.0 mL/min |
| Detection: | UV @ 220 nm |
| Injection volume | 20 μL |

Typical retention times are given in the following table:

| Name of the compound | | Typical Retention time, min |
|---|---|---|
| 1-Palmitoyl-lysolecithine | (potential impurity) | 6 |
| 1-Stearoyl-lysolecithine | (potential impurity) | 8 |
| 1-Palmitoyl-DP-VPA | | 12 |
| 1-Stearoyl-DP-VPA | | 18 |

A typical HPLC chromatogram of $C_{16}$-DP-VPA/$C_{18}$-DP-VPA mixture at a ratio of 15%:85% (by weight) which was analysed as described above is depicted in FIG. 1.

Example 4
Toxicology and Safety Studies in Humans

A Phase I safety and tolerability clinical trial has been carried out using $C_{16}/C_{18}$-DP-VPA mixture ($C_{16}$-DP-VPA/$C_{18}$-DP-VPA at a ratio of 15%:85% w/w) in solution of 5% Poloxamer F-127+0.5% Tween-80 and the oral route of administration.

The design of this study was double blind, placebo randomized. It was divided into a single administration part and a part in which there was repeated daily administration for 7 consecutive days. In each part the doses were increased at intervals of 7 days if the previous dose was well tolerated. Five doses ranging form 0.3125 g to 5 g of DP-VPA were administered as single doses in the first part of the study and 3 doses (0.3125 g, 0.625 g and 1.25 g) were administered as repeated doses in the second part of the study. Fifty six subjects in total were enrolled in this study: 29 in the first part and 27 in the second part.

In the first part, nausea and vomiting were the most commonly reported adverse effects, the incidence of which was highest in the highest dose group (DP-VPA 5 g) with 3 of the 6 subjects reporting it. Two of the 6 subjects in the second highest dose group (DP-VPA 2.5 g) reported nausea and vomiting. Headache, diarrhoea, abdominal pain and dizziness were also reported but in the investigator's opinion they were probably not study drug related. With regard to the laboratory results, vital signs and ECG parameters, no trends were seen and all results remained within acceptable parameters for all subjects.

In the second part, fewer adverse effects occurred and only 3 (burning stomach and abdominal pain) were considered to be probably related to the drug as they occurred soon after administration. There were no incidences of nausea and the 1 episode of vomiting occurred more than 24 h after administration and was not related to the study drug.

From the point of view of the vital signs, ECGs, laboratory tests, urinalysis and physical examinations the tolerability was very good.

Conclusions: In both the single and repeated administration parts of this study the clinical and biological tolerability was found to be very good at DP-VPA doses of up to 2.5 g. It can be concluded that the DP-VPA's toxicological profile is significantly improved compared to that for the parent drug VPA.

Example 5
Pharmacokinetics Studies in Humans

In order to assess the pharmacokinetic properties of the $C_{16}$-DP-VPA and $C_{18}$-DP-VPA compounds, the plasma levels of these compounds were monitored in human subjects.

Healthy male volunteers, 18–40 year old, (7 individuals for each dose tested) received, by a single oral administration, 0.3125 g, 0.625 g or 1.25 g of $C_{16}/C_{18}$-DP-VPA mixture at a ratio of $C_{16}/C_{18}$=13%:87% (w/w). Blood samples, 10 ml each, were drawn from each individual at the time points after the administration of the drug, as indicated. The samples were centrifuged at 4° C. at 1100 g for 10 minutes immediately after collection. Plasma levels of $C_{16}$-DP-VPA and $C_{18}$-DP-VPA were determined using a LC-MS/MS technique. The plasma concentration profiles of $C_{16}$-DP-VPA and $C_{18}$-DP-VPA as monitored for 24 hours following a single oral administration 0.625 g of $C_{16}/C_{18}$-DP-VPA are shown, respectively, in FIGS. 2A and 2B.

As can be seen from the results of the human study, the $C_{16}$-DP-VPA and $C_{18}$-DP-VPA compounds have different kinetic profiles. While the peak concentration of $C_{16}$-DP-VPA in the plasma was reached at 6 hours after the administering of the drug, the peak of $C_{18}$-DP-VPA was reached two hours later, at 8 hours post administration.

The terminal plasma half-life ($t_{1/2}$) for the $C_{16}$-DP-VPA and $C_{18}$-DP-VPA compounds was calculated form their plasma concentration-time profiles. It was found that the calculated $t_{1/2}$ values for the two compounds were significantly different; $t_{1/2}$ for $C_{16}$-DP-VPA was 14.0±0.6 hours compared to 8.3±1.3 hours for $C_{18}$-DP-VPA.

The $t_{1/2}$ measured for the global DP-VPA was 10.6±1.2 hours, a value that combines the pharmacokinetic profiles of both the $C_{16}$-DP-VPA and $C_{18}$-DP-VPA compounds.

Plasma concentration ($\mu$g/ml) of $C_{16}$-DP-VPA and of $C_{18}$-DP-VPA measured in samples collected at various time points following a single oral administration of 0.625 g $C_{16}/C_{18}$-DP-VPA are summarized in Table 1.

TABLE 1

$C_{16}$-DP-VPA and of $C_{18}$-DP-VPA concentrations in humans plasma following a single oral administration of $C_{16}/C_{18}$-DP-VPA.

| Time (hours) | $C_{16}$-DP-VPA ($\mu$g/ml) | $C_{18}$-DP-VPA ($\mu$g/ml) | Ratio $C_{18}/C_{16}$ |
|---|---|---|---|
| 1 | 0.013 ± 0.034 | 0.000 ± 0.000 | |
| 3 | 0.167 ± 0.094 | 0.058 ± 0.043 | 0.35 |
| 6 | 0.397 ± 0.172 | 0.818 ± 0.292 | 2.1 |
| 8 | 0.385 ± 0.140 | 1.175 ± 0.137 | 3.1 |
| 10 | 0.368 ± 0.182 | 0.949 ± 0.254 | 2.6 |
| 12 | 0.318 ± 0.150 | 0.698 ± 0.163 | 2.2 |

As can be seen from the results in Table 1, the observed ratios of $C_{18}$-DP-VPA/$C_{16}$-DP-VPA were different from the expected ratio of 6.7 ($C_{18}$-DP-VPA: $C_{16}$-DP-VPA ratio 87%:13% (by weight)).

Surprisingly, the presentation of the $C_{16}$-DP-VPA compound in the plasma was found to be higher than its proportion in the administered mixture. This phenomenon was more pronounced at the shorter time points, i.e. less than 6 hours following the administration of $C_{16}/C_{18}$-DP-VPA.

The highest ratio of $C_{18}/C_{16}$, i.e. 3.1 (which is still below the expected ratio of 6.7) was reached at 8 hours following the administration of $C_{16}/C_{18}$-DP-VPA. At this point the levels of $C_{18}$-DP-VPA reach their peak concentration in the plasma.

These observations indicate that the $C_{16}$-DP-VPA and $C_{18}$-DP-VPA compounds demonstrate different pharmacokinetic profiles.

Example 6
Anti-convulsive Effect of $C_{16}$-DP-VPA; $C_{18}$-DP-VPA and $C_{16}/C_{18}$-DP-VPA Mixtures (efficacy study)

The anti-epileptic efficacies of $C_{16}$-DP-VPA, $C_{18}$-DP-VPA and mixtures comprising both $C_{16}$-DP-VPA and $C_{18}$-DP-VPA were evaluated in mice. The protective effect of the compounds was compared at different time points following chemical seizure induction by pentylenetetrazol (PTZ).

The pentylenetetrazol (PTZ) induced seizure model in mice is an established animal model system for epilepsy. Subcutaneous injection of PTZ into control animals results in the following sequence of events: myoclonic jerks within 1–2 mins, followed by clonic and clonic-tonic seizures each lasting approximately 5–10 secs with the severity of seizures increasing with time for up to 30 mins. 80% of the first seizures are observed within 5 mins, and 100% within 20 mins. The second seizures usually follow within 6–10 mins and subsequent seizures (if any) every 6 mins.

CD-1 mice (25–30 g) were pre-treated by subcutaneous (s.c.) injection of either $C_{16}$-DP-VPA or $C_{18}$-DP-VPA or a mixture thereof The amounts used were equivalent to 40 mg/kg VPA. After different times as indicated, 1, 2 or 4 hours, a convulsive dose of pentylenetetrazol (85–100 mg/kg ) was subcutaneously injected into the mice. The animals were monitored for one hour following the PTZ administration for the occurrence of episodes of clonic spasms persisting for at least 5 sec. The protection effect was calculated as the number of animals that did not experience a second seizure divided by the total number of animals tested.

In Tables 2 A–D are shown the results of PTZ-induced seizures test as described above, wherein the tested compositions were as follows:

Table A—$C_{16}$-DP-VPA 100%
Table B—$C_{16}$-DP-VPA/$C_{18}$-DP-VPA ratio 50/50 (by weight)
Table C—$C_{16}$-DP-VPA/$C_{18}$-DP-VPA ratio 10/90 (by weight)
Table D—$C_{18}$-DP-VPA 100%
n=the number of animals experiencing a seizure;
N=the total number of animals in the assay.

TABLES 2 A–D

PTZ-induced seizures test in mice

| Time (h) | Second seizure (n//N) | % Protection |
|---|---|---|
| A) $C_{16}$-DP-VPA-100% | | |
| 1 | 4/8 | 50 |
| 2 | 6/8 | 25 |
| 4 | 5/8 | 38 |
| B) $C_{16}$-DP-VPA/$C_{18}$-DP-VPA: 50/50 | | |
| 1 | 6/7 | 14 |
| 2 | 6/7 | 14 |
| 4 | 5/8 | 38 |
| C) $C_{16}$-DP-VPA/$C_{18}$-DP-VPA: 10/90 | | |
| 1 | 5/7 | 29 |
| 2 | 6/7 | 14 |
| 4 | 2/8 | 75 |
| D) $C_{18}$-DP-VPA-100% | | |
| 1 | 5/6 | 17 |
| 2 | 6/7 | 14 |
| 4 | 1/7 | 86 |

As can be seen in Table 2, the $C_{18}$-DP-VPA compound is more effective in prevention of second seizures, showing 86% protection compared to a maximum of 50% protection obtained by 100% $C_{16}$-DP-VPA.

The $C_{16}$-DP-VPA/$C_{18}$-DP-VPA mixtures demonstrated intermediate behaviour, with the effect of the $C_{16}$-DP-VPA/$C_{18}$-DP-VPA at a ratio of 10/90 (Table C) being closer to that obtained with the pure $C_{18}$-DP-VPA compound. However, protection was more apparent at 1 hour with the 10/90 mixture than with 100% $C_{18}$-DP-VPA.

It is also important to note the different kinetics of the protective effects by the two DP-VPA compounds. The peak activity of $C_8$-DP-VPA was obtained 4 hours after the administration of PTZ, while the pure $C_{16}$-DP-VPA reached its maximal therapeutic effect already within 1 hour.

Conclusion: although $C_{16}$-DP-VPA and $C_{18}$-DP-VPA have similar potency as anti-convulsant (i.e. similar $ED_{50}$ values), their therapeutic profiles are different. The $C_{16}$-DP-VPA compound is more effective in preventing seizures in the first hour after induction of seizures by subcutaneous administration of PTZ. The $C_{18}$-DP-VPA compound, on the other hand, shows maximal anti-convulsant activity at the later times, i.e. at four hours after the injection of PTZ (see Table A in comparison to Table D).

It is important to note that the tested $C_{16}$-DP-VPA/$C_{18}$-DP-VPA mixtures, in particular the $C_{16}/C_{18}$ mixture at a ratio of 10:90, behave in a similar way to the 100% $C_{18}$-DP-VPA compound, namely demonstrating high maximal seizure protection, but over a more prolonged time.

Example 7

Suitable Formulations for Administration of DP-VPA

The DP-VPA compounds and compositions of the present invention can be administered to a subject in a number of ways, which are well known in the art. For example, administration may be done orally, parenterally, (for example by intravenous drip or intraperitoneal, subcutaneous, or intramuscular injection), topically, (for example by nasal application or inhalation) or rectally.

Formulations for topical administration may include, but are not limited to drops, liquids, sprays, powders, suppositories, creams, gels and ointments. Conventional pharmaceutical carriers, aqueous, powder or oily bases, thickeners and the like may be necessary or desirable.

Formulations for parenteral administration may include, but are not limited to, sterile aqueous solutions which may also contain buffers, diluents and other suitable additives.

Compositions for oral administration may be formulated as powders or granules, suspensions or solutions in water or non-aqueous media, in the dosage form of tablets, capsules, syrups or solutions. The formulation may be designed so to enable modified controlled release of the active agent. The capsules and tablets may be coated so to afford site-specific delivery to different parts of the gastrointestinal tract. Thickeners, diluents, flavorings, dispersing aids, emulsifiers or binders may be desirable.

Suitable pharmaceutical excipients that may be included in the formulations include, but are not limited to, phospholipids, triglycerides, propylene glycols, polyethylene glycols, poloxamers, surfactant and co-surfactants.

Dosing is dependent on the severity of the symptoms and on the responsiveness of the subject to the DP-VPA drug. Persons of ordinary skill in the art can easily determine optimum dosages and dosage form as well as dosage regimen and means of administration.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. A method for the treatment of a central nervous system disorder in a mammal comprising administering to a mammal in need of treatment, a pharmaceutical composition comprising a therapeutically effective amount of valproic acid or pharmaceutically acceptable derivative thereof covalently bonded to a phospholipid moiety; a pharmaceutically acceptable carrier; said composition providing a therapeutic effect after administration.

2. The method according to claim 1, wherein the central nervous system disorder is selected from epilepsy, migraine, bipolar disorders and pain.

3. The method according to claim 1, wherein the central nervous system disorder is epilepsy.

4. The method according to claim 1, wherein said said phophoslipid moiety is 1-stearoyl-sn-glycero-3-phosphorylcholine.

5. The method according to claim 1, wherein said said phophoslipid moiety is 1-palmitoyl-sn-glycero-3-phosphorylcholine.

6. A pharmaceutical composition comprising a therapeutically effective amount of valproic acid or pharmaceutically acceptable derivative thereof covalently bonded to a phospholipid moiety; and a pharmaceutically acceptable carrier.

7. The pharmaceutical composition according to claim 6, wherein said phospholipid moiety is selected from the group consisting of plasmalogens, phosphatidic acids and phospho-esters derivatives thereof.

8. The pharmaceutical composition according to claim 6, wherein said phospholipid moiety is selected from the group consisting of lysophosphatidyl-ethanolamine, N-mono-($C_{1-4}$)-alkyl, N,N-di-($C_{1-4}$)-alkyl and quaternary derivatives of the amines thereof.

9. The pharmaceutical composition according to claim 8, wherein said quaternary derivative of lysophosphatidyl-ethanolamine is lysophosphatidylcholine.

10. The pharmaceutical composition according to claim 6, wherein said valproic acid or pharmaceutically acceptable derivative thereof covalently bonded to said phospholipid moiety is 1-palmitoyl-2-valproyl-sn-glycero-3-phosphatidyl-choline.

11. The pharmaceutical composition according to claim 6, wherein said valproic acid or pharmaceutically acceptable derivative thereof covalently bonded to said phospholipid moiety is 1-stearoyl-2-valproyl-sn-glycero-3-phosphatidyl-choline.

12. The pharmaceutical composition according to claim 6 wherein said valproic acid or pharmaceutically acceptable derivative thereof is covalently linked to said phospholipid moiety at a position selected from the group consisting of sn-1, sn-2, and sn-3.

13. The pharmaceutical composition according to claim 6 wherein said valproic acid or pharmaceutically acceptable derivative thereof is covalently linked to said phospholipid moiety at a position sn-2.

14. The pharmaceutical composition according to claim 13 wherein said valproic acid or pharmaceutically acceptable derivative thereof is released by cleavage by phospholipase $A_2$ at said sn-2 position.

15. The pharmaceutical composition according to claim 6, wherein said composition is in a form selected from the group consisting of solutions, suspensions, emulsions, syrups, capsules, tablets and suppositories.

16. The pharmaceutical composition of claim 6, which is suitable for oral administration, intravenous administration, or rectal administration.

17. The pharmaceutical composition of claim 6, further comprising a second valproic acid or pharmaceutically acceptable derivative thereof covalently bonded to a different phospholipid moiety;
wherein said valproic acid or pharmaceutically acceptable derivative thereof covalently bonded to said phospholipid moiety and said second valproic acid or pharmaceutically acceptable derivative thereof covalently bonded to said different phospholipid moiety are in a ratio of from about 1:20 to about 1:2 by weight.

18. The pharmaceutical composition of claim 6, further comprising a second valproic acid or said pharmaceutically acceptable derivative thereof covalently bonded to a different phospholipid moiety;
wherein said valproic acid or pharmaceutically acceptable derivative thereof covalently bonded to said phospholipid moiety and said second valproic acid or pharmaceutically acceptable derivative thereof covalently bonded to said different phospholipid moiety are in a ratio of from about 1:5 to about 1:7 by weight.

19. The pharmaceutical composition of claim 6, further comprising a second valproic acid or a pharmaceutically acceptable derivative thereof covalently bonded to a different phospholipid moiety.

20. The pharmaceutical composition of claim 19, wherein said valproic acid or pharmaceutically acceptable derivative thereof covalently bonded to said phospholipid moiety is 1-palmitoyl-2-valproyl-sn-glycero-3-phosphatidyl-choline.

21. The pharmaceutical composition of claim 19, wherein said second valproic acid or pharmaceutically acceptable derivative thereof covalently bonded to said different phospholipid moiety is 1-stearoyl-2-valproyl-sn-glycero-3-phosphatidyl-choline.

22. The pharmaceutical composition of claim 19, wherein the total amount of said first valproic acid or said pharmaceutically acceptable derivative thereof covalently bonded to said phospholipid moiety and said second valproic acid or said pharmaceutically acceptable derivative thereof covalently bonded to said different phospholipid moiety is from about 35 mg to about 2500 mg.

23. The pharmaceutical composition of claim 19, wherein the total amount of said first valproic acid or said pharmaceutically acceptable derivative thereof covalently bonded to said phospholipid moiety and said second valproic acid or said pharmaceutically acceptable derivative thereof covalently bonded to said different phospholipid moiety is from about 70 mg to about 560 mg.

24. The pharmaceutical composition of claim 19, wherein said combination exhibits greater therapeutic effects, prolonged therapeutic effects, or greater and prolonged therapeutic effects, on central nervous system disorders than a composition comprising only said valproic acid or pharmaceutically acceptable derivative thereof covalently bonded to a phospholipid moiety, or only said second valproic acid or pharmaceutically acceptable derivative thereof covalently bonded to said different phospholipid moiety.

25. The pharmaceutical composition of claim 19, wherein said valproic acid or pharmaceutically acceptable derivative thereof covalently bonded to said phospholipid moiety is 1-palmitoyl-2-valproyl-sn-glycero-3-phosphatidyl-choline and said second valproic acid or pharmaceutically acceptable derivative thereof covalently bonded to said different phospholipid moiety is 1-stearoyl-2-valproyl-sn-glycero-3-phosphatidyl-choline.

26. The pharmaceutical composition of claim 25, wherein 1-palmitoyl-2-valproyl-sn-glycero-3-phosphatidyl-choline and 1-stearoyl-2-valproyl-sn-glycero-3-phosphatidyl-choline are in a ratio of from about 1:20 to about 1:2 by weight.

27. The pharmaceutical composition of claim 25, wherein 1-palmitoyl-2-valproyl-sn-glycero-3-phosphatidyl-choline and 1-stearoyl-2-valproyl-sn-glycero-3-phosphatidyl-choline are in a ratio of from about 1:5 to about 1:7 by weight.

28. The pharmaceutical composition of claim 25, which is suitable for oral administration, intravenous administration, or rectal administration.

29. A method of reducing side effects of valproic acid or pharmaceutically acceptable derivative thereof by administering said valproic acid or pharmaceutically acceptable derivative in the form of a composition as claimed in claim 6.

30. A method of reducing interactions of valproic acid or pharmaceutically acceptable derivative thereof with other therapeutic agents by administering said valproic acid or pharmaceutically acceptable derivative in the form of a composition as claimed in claim 6.

31. A method of increasing valproic acid or pharmaceutically acceptable derivative thereof efficacy by administering said valproic acid or pharmaceutically acceptable derivative in the form of a composition as claimed in claim 6.

32. A compound comprising valproic acid or pharmaceutically acceptable derivative thereof covalently bonded to a phospholipid moiety.

33. The compound of claim 32 wherein said phophoslipid moiety is 1-stearoyl-sn-glycero-3-phosphorylcholine.

34. The compound of claim 32 wherein said phophoslipid moiety is 1-palmitoyl-sn-glycero-3-phosphorylcholine.

* * * * *